United States Patent [19]

Quallich

[11] Patent Number: 5,539,128
[45] Date of Patent: Jul. 23, 1996

[54] PROCESSES AND INTERMEDIATES FOR PREPARING CIS(+)3-[4,6-DIHYDROXY CHROMAN-3-YLMETHYL]-4-METHOXYANILINE

[75] Inventor: George J. Quallich, North Stonington, Conn.

[73] Assignee: Pfizer Inc., New York, N.Y.

[21] Appl. No.: 346,955

[22] Filed: Nov. 30, 1994

[51] Int. Cl.⁶ .................................................. C07D 311/28
[52] U.S. Cl. ................................................................ 549/401
[58] Field of Search .............................................. 549/401

[56] References Cited

U.S. PATENT DOCUMENTS

| | | | |
|---|---|---|---|
| 4,661,596 | 4/1987 | Kreft et al. | 546/152 |
| 5,059,609 | 10/1991 | Eggler et al. | 514/314 |

OTHER PUBLICATIONS

Hackh's Chem. Dictionary pp. 398 and 470 (1987).
Hannon, S. J. et al 'A new synthesis of N–blocked dihydrouracil and dihydroorotic acid derivatives using lithium tri–sec–butyl borohydride as reducing agent' CA:30689q 1981.

*Primary Examiner*—Amelia Owens
*Attorney, Agent, or Firm*—Peter C. Richardson; Paul H. Ginsburg; Seymour G. Bekelnitzky

[57] ABSTRACT

Processes, and intermediates, for use in preparing the compound of the formula

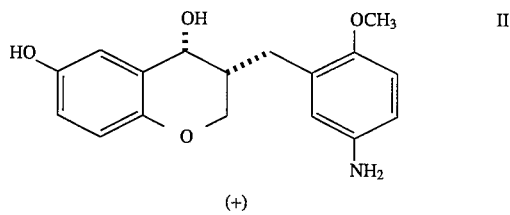

The compounds of formula II are useful in the preparation of cis (+) N-trifluoromethylsulfonyl-3-[4-hydroxy-6-ArO-chroman-3-ylmethyl]-4-methoxyaniline compounds wherein Ar is defined below. The cis (+) N-trifluoromethylsulfonyl-3-[4-hydroxy-6-ArO-chroman-3-ylmethyl]-4-methoxyaniline compounds are useful for inhibiting the production of leukotrienes and/or blocking leukotriene receptors and in the prevention or treatment of asthma, arthritis, psoriasis, ulcers, myocardial infarction and related disease states in mammals.

15 Claims, No Drawings

PROCESSES AND INTERMEDIATES FOR PREPARING CIS(+)3-[4,6-DIHYDROXY CHROMAN-3-YLMETHYL]-4-METHOXYANILINE

BACKGROUND OF THE INVENTION

The present invention is related to compounds of the formula

Ar—CH$_2$O— [chroman structure with OH] —CH$_2$— [phenyl with CH$_3$O and NHSO$_2$CF$_3$]   I (+)

wherein Ar is an optionally substituted 5–8 membered heteroaryl or optionally substituted benzene fused optionally substituted heteroaryl ring wherein said heteroaryl ring comprises 1 to 4 heteroatoms selected from nitrogen, oxygen and sulfur;

and pharmaceutically acceptable salts and prodrugs therefor (hereafter "the active compounds").

More particularly it relates to processes and intermediates useful in the preparation of the compound of the formula HO— [chroman structure with OH] —CH$_2$— [phenyl with OCH$_3$ and NH$_2$]   II (+)

which are intermediates useful in the preparation of compounds of the formula I.

The active compounds, which are disclosed in International Patent application no. PCT/US93/09171 (the '171 application) (assigned to the Assignee of this application and incorporated herein by reference), inhibit the production of leukotrienes and/or block leukotriene receptors and are useful in the prevention or treatment of asthma, arthritis, psoriasis, ulcers, myocardial infarction and related disease states in mammals.

U.S. Pat. No. 4,661,596, refers to compounds which are disubstituted naphthalenes, dihydronaphthalenes or tetralins having the formula R$^a$—O— [naphthalene structure] —R$^b$ wherein the dotted lines represent optional double bonds, R$^a$ is 2-pyridyl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and R$^b$ is hydroxy, lower alkoxy, lower alkyl or perfluoro alkyl.

U.S. Pat. No. 5,059,609 refers to substituted tetralins, chromans and related compounds.

The compounds of these patents are alleged to inhibit lipoxygenase enzyme and antagonize the effects of leukotriene D4 and, therefore, to be useful in the prevention and treatment of asthma.

SUMMARY OF THE INVENTION

The present invention relates to processes and intermediates useful in the preparation of the compound of the formula II, above. More particularly, the invention relates to a process for the preparation of the compound of formula II which comprises the steps of a) treating the compound of the formula

[Ph-CH$_2$O-chromanone-CH$_2$-phenyl(OCH$_3$)(NH$_2$)]   V with L-Selectride (trademark) commonly known as lithium tri-sec-butyl borohydride or NaBH$_4$ and CeCl$_3$, to form the compound of the formula

[Ph-CH$_2$O-chroman(OH)-CH$_2$-phenyl(OCH$_3$)(NH$_2$)]   IVB (±)

and treating the compound of formula IVB with (R) camphorsulfonic acid, [(R)-CSA],

[Ph-CH$_2$O-chroman(OH)-CH$_2$-phenyl(OCH$_3$)(NH$_2$·(R)—CSA)]   IVA (±)

b) 1) treating the compound of the formula IVA with a base, preferably Na$_2$CO$_3$, to again form the the compound of the formula IVB and ii) treating the compound of formula IVB formed in this step, with ditoluyl-L-tartaric acid [L-DTTA] to form the compound of the formula

[Ph-CH$_2$O-chroman(OH)-CH$_2$-phenyl(OCH$_3$)(NH$_2$·L—DTTA)]   IIIB (+)

or 2) treating the compound of formula IVA with hot acetone to isolate the compound of the formula

[Ph-CH$_2$O-chroman(OH)-CH$_2$-phenyl(OCH$_3$)(NH$_2$(R)—CSA)]

(+)

and c) treating the compound of formula IIIB or IIIC with a base to form the compound of the formula

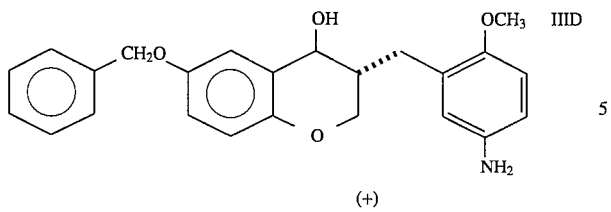

(+)

and then treating the compound of the formula IIID with $H_2$ over a noble metal catalyst, preferably $Pd(OH)_2$, to form the compound of formula II.

The invention further comprises a compound selected from the group consisting of

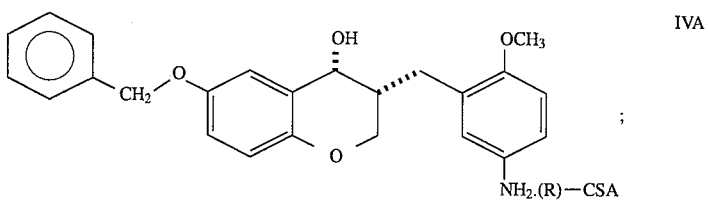

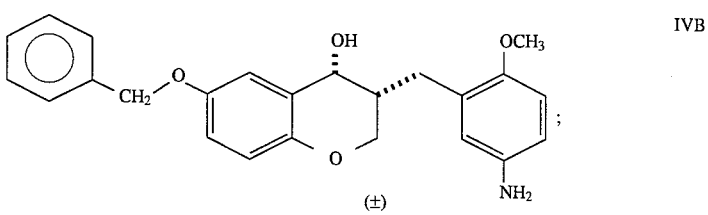

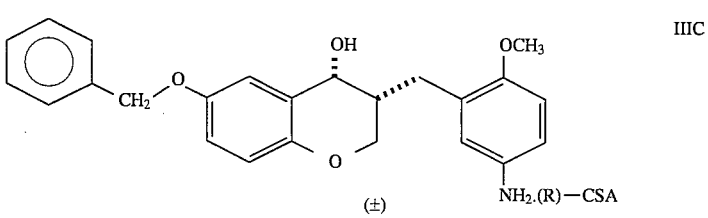

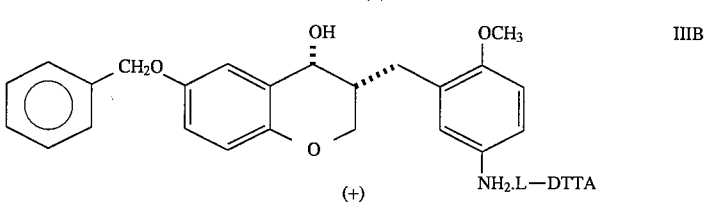

and

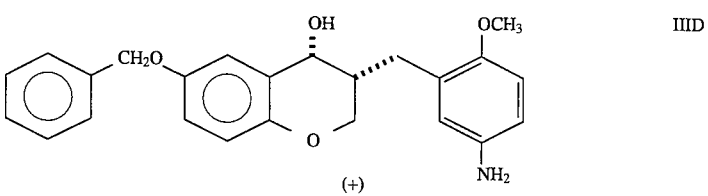

DETAILED DESCRIPTION OF THE INVENTION

The preparation of the compound of formula II, and certain of the starting materials used therein, is illustrated in the following reaction scheme.

All articles, books, patents and patent applications cited in the following discussion are incorporated herein by reference.

SCHEME
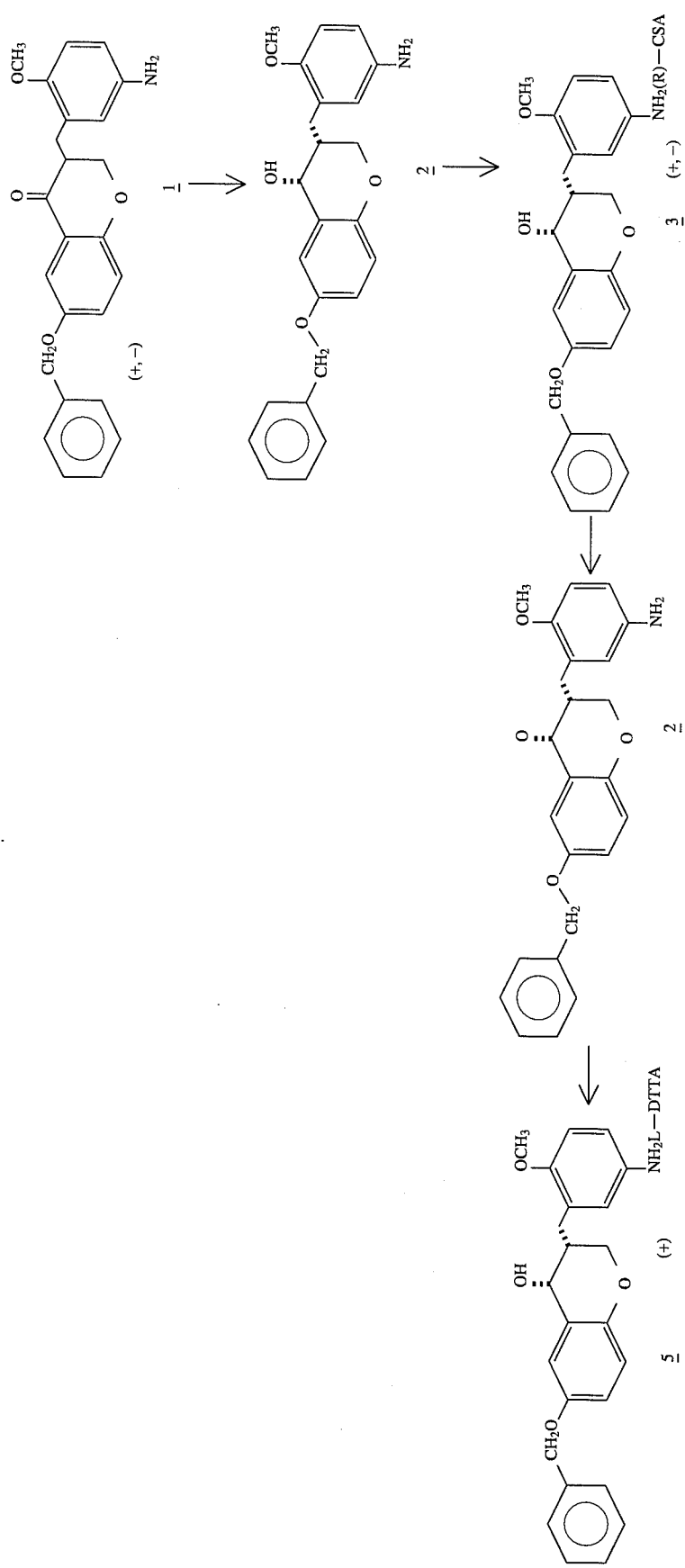

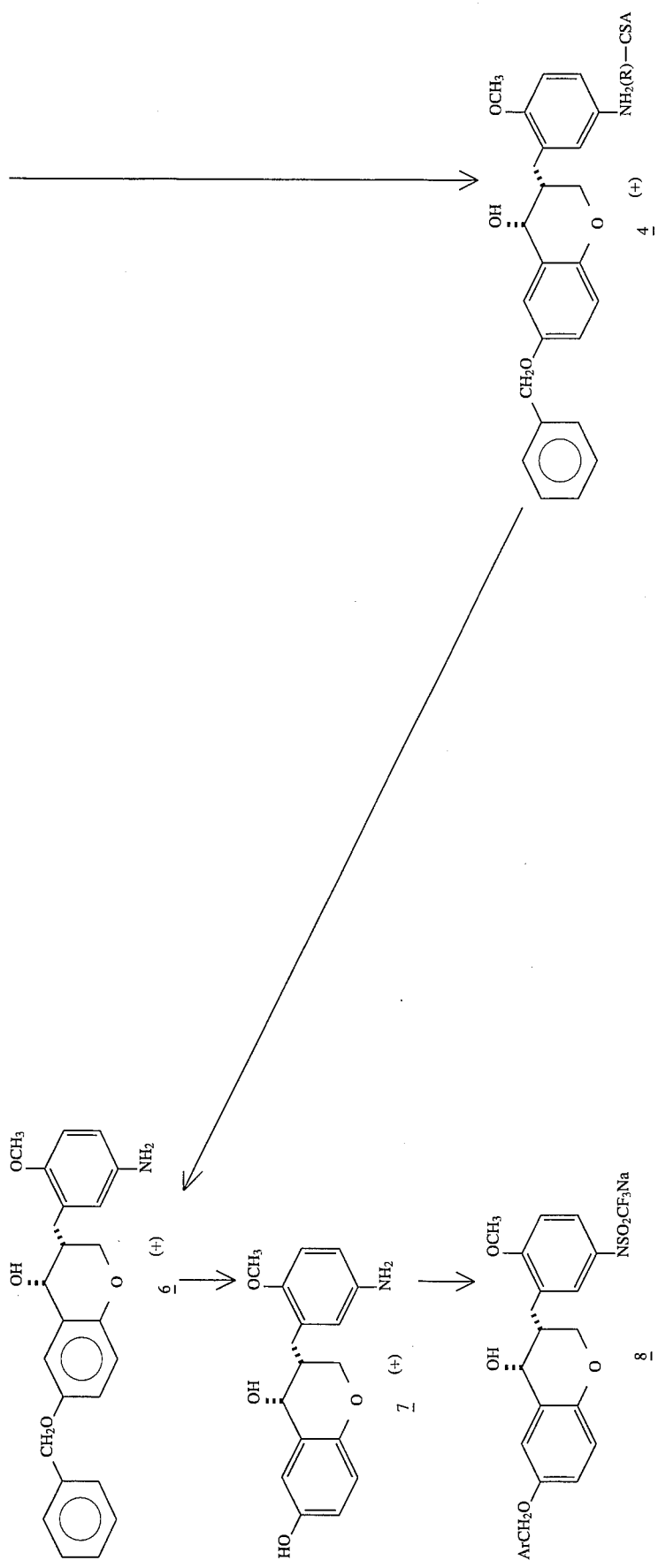
-continued
SCHEME wherein Ar is as defined above.

Compound 1 is converted to compound 2 by treatment with a hydride reducing agent. Preferred reducing agents are $CeCl_3/NaBH_4$ and L-Selectride. When $CeCl_3/NaBH_4$ is used as the reducing agent the reduction is effected in solvents such as alcohols, and ethers and mixtures thereof. With this reducing agent there are no temperature or pressure conditions. The only condition is that none of the solvents be reactive with the reactants or products of the reaction. A preferred solvent is a mixture of methanol and THF. When L-Selectride is the reducing agent the reduction is preferably effected at a temperature below about 0° C. in an inert atmosphere. Preferably the reduction is effected at a temperature between about −70° and about −80° C. in an inert atmosphere such as dry nitrogen or argon. The most preferred reducing agent is L-Selectride which is used at a temperature below about −70° C. in a nitrogen atmosphere. Compound 1 is prepared, from known starting materials, by methods known to the art.

Compound 3 is prepared by treating compound 2 with (R)—camphorsulfonic acid. The reaction is is effected at a temperature between about −20° and about +50° C. in a polar solvent such as an ether, ester or alcohol. Preferably the reaction is effected at room temperature in ethyl acetate. Compound 2 need not be isolated from the reaction mixture, of the previous step, and this procedure may be effected directly thereon.

Preparation of compound 5 from compound 3 is effected by treatment of compound 3 with an inorganic base such as a hydroxide, carbonate or bicarbonate of an alkali metal, such as sodium or potassium, or an alkaline earth metal, such as calcium or magnesium in a mixture of water and a polar solvent such as an ester or ether to regenerate compound 2. Preferably the reaction is effected in a mixture of water and ethyl acetate. A preferred base is sodium bicarbonate. Compound 2 is then treated with L-DTTA in ethyl acetate to form compound 5. The reaction may be effected at a temperature between about 0° and about 78° C., preferably at room temperature. Compound 2 need not be isolated from the reaction mixture, of the previous step, and this procedure may be effected directly thereon.

Compound 5 is converted to compound 6 under the same conditions as for the conversion of compound 3 to compound 2, above. Compound 6 need not be isolated from the reaction mixture which may be directly be used in the following hydrogenolysis step.

Alternatively, compound 3 may be converted to compound 6 by the following method. Compound 4 is obtained by resolution of compound 3 by in hot acetone. A preferred resolving agent is aqueous acetone wherein the ratio of acetone to water is from about 85:15 to about 99:1. A preferred acetone:water ratio is 93:7. Compound 3 is disssolved in hot aqueous acetone at about 50° to 55° C. and upon cooling the solution the desired, less soluble, compound 4 crystallizes. Compound 4 is then converted to compound 6 by treatment with a base, under the same conditions as indicated, above, for the conversion of compound 5 to compound 6 and the reaction mixture may be directly used in the next step without prior isolation of compound 6.

Compound 6 is converted to compound 7 by reduction with hydrogen in the presence of a noble metal hydrogenolysis catalyst. A preferred hydrogenolysis catalyst is $Pd(OH)_2$. Preferably the reaction is effected at a hydrogen pressure of from about 15 to about 100 psi in the presence of a solvent such as a lower alkanol, ether or ester at room temperature, Most preferably the reduction is effected at a pressure of about 40 psi in a solvent comprising a mixture of methanol and ethyl acetate. Most preferably the solvent consists of methanol.

Compound 7 can be converted to compound 8 by the methods described in Examples 9 and 10, below, or in Example 18 of the '171 patent.

For use in the prevention or treatment of asthma, arthritis, psoriasis and gastrointestinal ulcers in a mammal, including man, a compound of the formula I is given in a 5-lipoxygenase inhibiting and/or leukotriene receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The active compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in, e. g., the U.S. Pat. Nos. 4,256,108; 4,166,452; and 4,265,874 to form osmotic therapeutic tablets for control release.

The hard capsules for oral use may also be presented as gelatin capsules wherein the active ingredient is mixed with an inert solid diluent, for example, calcium carbonate, calcium phosphate or kaolin, or whereas the soft capsules may be presented as gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinyl pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents may also be present.

The pharmaceutical compositions of the invention may also be in the form of oil-in water emulsions. The oily phase may be a vegetable oil, for example, olive oil or arachis oil; a mineral oil such as liquid paraffin or mixtures of these. Suitable emulsifying agents may be naturally occurring gums, for example, gum acacia or gum tragacanth; naturally-occurring phosphatides such as example soy bean and lecithin; and esters or partial esters derived from fatty acids and hexitol anhydrides, for example, sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulation may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The active compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, creams, ointments, Jellies, solutions or suspensions, etc., containing the active compounds of the invention are employed.

For administration by inhalation, the active compounds of the invention are conveniently delivered in the form of an aerosol spray presentation from pressurized packs or a nebulizer. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

The amount of active ingredient that may be combined with the carrier materials to produce a single dosage form will vary depending upon the host treated and the particular mode of administration. Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The present invention is illustrated by the following examples, but is not limited to the details thereof.

EXAMPLE 1

3-[4-Oxo-6-benzyloxychroman-3-ylidenemethyl]-4-methoxynitrobenzene

A suspension of 6-benzyloxychroman-4-one (448.96 g, 1.77 mol) in a methanolic (6.9 L) solution containing 2-methoxy-4-nitrobenzaldehyde (319.98 g, 1.77 mole) and pyrrolidine (147.19 mL, 1.77 mol), was heated to 50° C. for 24 hours. The reaction mixture was allowed to cool to 22° C. over 18 hours. The solid yellow product was isolated by filtration. Yielded (dry weight) 657.55 g (89%). Mp=156°–57° C. $^{13}$C NMR δ 181.7, 162.7, 156.1, 153.7, 140.9, 136.6, 133.1, 130.9, 128.6, 128.1, 127.6, 126.8, 126.0, 125.6, 124.1, 121.8, 119,4, 110.7, 109.6, 70.6, 67.6, 56.5;

EXAMPLE 2

3-[4-Oxo-6-benzyloxychroman-3-ylmethyl]-4-methoxyanilline

The title compound of Example 1 (35.41 g, 85 mmol), dissolved in tetrahydrofuran (THF) (1.5 L), was hydrogenated at 50 psi, for 4 hours, over 5% Pt on C (7.08 g, 50% water wet), The reaction mixture was filtered through Celite (trademark). The volume of the reaction mixture, was reduced, by vacuum distillation, to 140 mL and 210 mL isopropyl ether (IPE)) was then added to the reactor. 210 mL of solvent was then removed, by vacuum distillation, and 210 mL of IPE was added to the reactor. Another 140 mL of solvent was then removed, by vacuum distillation, and 500 mL of IPE was added to the reactor. The product began crystallizing and heating was stopped. The reaction mixture was allowed to cool to 24° C. over 16 hours. The off white solid product was collected by vacuum filtration and dried to afford 27.42 g (83%). $^{13}$C NMR [(CD$_3$)$_2$SO] δ 193.6, 156.1, 153.0, 149.2, 142.5, 137.4, 128.9, 128.3, 128.0, 126.9, 125.4, 120.6, 119.5, 117.4, 113.4, 112.5, 109.6, 70.1, 56.0, 45.8, 27.4, 23.2.

EXAMPLE 3 cis(+)3-[4-Hydroxy-6-benzyloxychroman-3-ylmethyl]-4-methoxyanilline (R)-camphorsulfonic acid salt A. Cerium trichloride heptahydrate (766.2 g, 2.05 mmol) was added to a tetrahydrofuran (7L)/methanol (2.4 L) solution of the title compound of Example 2 (400 g, 1.02 mole). The reaction mixture was cooled to <−70° C., and sodium borohydride (38.88 g, 1.02 mole) was added in four portions at five minute intervals. The reduction was completed by TLC in 1.5 hours and the reaction mixture was stirred an additional 18 hours during which time it was warmed to 23° C. Acetone (600 mL) was added and the reaction mixture was stirred 1 hour to quench any remaining borohydride. The solvents were removed under vacuum and chased 2 times with 800 mL with ethyl acetate. Ethyl acetate (4 L), saturated ammonium chloride (2550 mL), and Celite (50 g,) were added and the reaction mixture was stirred 15 minutes. The mixture was filtered through Celite, the liquid phases were separated and the ethyl acetate layer was washed with water (2550 mL). The organic phase was treated with magnesium sulfate, and the volume reduced under vacuum to 4 L. (R)-camphorsulfonic acid (214.98 g, 0.925 mole) was added and a solid precipitated within 15 minutes. The resultant mixture was stirred overnight and filtered. The precipitate was washed with acetone (1.8 L) and dried under vacuum. A white solid was isolated, yield: 516 g, 80%. This material contained about 15% of the trans isomer. Removal of the trans isomer was achieved by slurrying in methanol (2.5 L) for 18 hours. The residue was filtered and dried to yield the title compound as a white solid (382.8 g, 74%).

B. The title compound was also prepared as follows. The title compound of Example 2 (3.0 g, 7.71 mmol) was dissolved in THF (50 mL) and cooled to about or less than −70° C. L-Selectride (trademark) commonly known as lithium tri-sec-butyl borahydride (1 M, 11 mL, 11 mmol) was added dropwise while maintaining the temperature at about, or less than, −70° C. The reaction mixture was stirred for 45 minutes, trimethylamine N-oxide dihydrate (3.7 g, 33 mmol) was added and the cooling bath removed. After warming to 20° C., the reaction mixture was heated to reflux for 5 hours and stirred at 23° C. for 18 hours. Aqueous ammonium chloride and ethyl acetate were added. After separation of the phases the organic phase was washed with aqueous ammonium chloride and brine, treated with magnesium sulfate and the solvent evaporated to yield an oil (4.5 g). The oil was dissolved in methanol (6 mL) and ethyl acetate (54 mL). (R)-camphorsulfonic acid (1.7 g, 7.32 mmol) was added to the solution which was stirred for 3 hours during which time a precipitate was formed. The precipitate was recovered by filtration and dried to afford 3.68 g (77%) of the title compound as a white solid containing less than about 5% of the trans isomer.

EXAMPLE 4 cis(+)3-[4-Hydroxy-6-benzyloxychroman-3-ylmethyl]-4-methoxyanilline

The title compound of Example 3 (9 g) was suspended in ethyl acetate (90 mL) and treated two times with 30 mL aqueous sodium carbonate. The aqueous layer was washed with water (30 mL) and dried over magnesium sulfate. The solvent was removed, under vacuum, to yield the title compound as a thick yellow oil. $^{13}$C NMR [(CD$_3$)$_2$SO]δ 152.2, 149.4, 148.3, 142.4, 137.9, 128.8, 128.5, 128.1, 128.0, 126.6, 117.5, 117.0, 116.5, 116.3, 112.9, 112.5, 70.1, 64.9, 6.46, 56.2, 38.9, 27.7.

EXAMPLE 5 cis(+)3-[4-Hydroxy-6-benzyloxychroman-3-ylmethyl]-4-methoxyanilline dituluyl-L-tartaric acid salt A. The title compound of Example 3 (40 g, 64 mmol) was suspended in ethyl acetate (400 mL) and the suspension was stirred twice with 700 mL aqueous saturated sodium bicarbonate. The ethyl acetate solution containing the aniline free base was washed with water (162 mL) and treated with magnesium sulfate. The volume was reduced, under vacuum, to 251 mL and the resulting solution treated with di-p-toluoyl-L-tartaric acid (24.28 g, 62.8 mmol). A precipitate formed immediately and the mixture was stirred for 18 hours and then filtered. The precipitate (36.9 g) was slurried twice with ethyl acetate (550 mL and 150 mL, respectively), and dried under vacuum to yield the title compound as a white solid (20.8 g, 84% of theory) which had no trans isomer and an enantiomeric purity of about 98.4%.

B. The title compound was also prepared as follows: The title compound of Example 3 (20 g, 32 mmol) was suspended in ethyl acetate (200 mL) and stirred twice with 323 mL aqueous saturated sodium bicarbonate. The ethyl acetate solution containing the aniline free base was washed with 81 mL water and dried with magnesium sulfate. The volume was reduced to 125 mL, under vacuum, and the resulting solution treated with di-p-toluoyl-L-tartaric acid (7.44 g, 19.2 mmole). A precipitate formed and the mixture was immediately stirred for 18 hours. The precipitate (10.59 g) was slurried in ethyl acetate (52 mL), and dried under vacuum to yield a white solid (8.65 g, 82% of theory) which had a trans isomer content of about 0.2% and an enantiomeric purity of about 98.6%.

C. Alternatively, the title compound of Example 3 is dissolved in ethyl acetate and treated, as indicated above in Sections A and B, with di-p-toluoyl-L-tartaric acid to form the title compound of this Example.

EXAMPLE 6 cis(+)3-[4-Hydroxy-6-benzyloxychroman-3-ylmethyl]-4-methoxyanilline

A suspension of the title compound of Example 5 (88 mg) in ethyl acetate was twice treated with 2 mL of saturated aqueous sodium carbonate. The organic layer was separated, washed with water (2 mL) and treated with magnesium sulfate. The solvent was removed, under vacuum to yield a thick oil. $[\alpha]_D$=+128.9 (c=0.35, CH$_3$OH).

EXAMPLE 7 cis(+)3-[4-Hydroxy-6-benzyloxychroman-3-ylmethyl]-4-methoxyanilline (R)-camphorsulfonic acid salt The title compound of Example 3 (13.4 g) was dissolved in acetone (405 mL) and water (54 mL) at 50° C. Complete solution was obtained after 45 minutes and the solution was then allowed to cool to ambient temperature and stirred for 18 hours. The title compound was isolated by vacuum filtration as a white solid (3.15 g, 23%) $[\alpha]_D$=+36.4 (C=0.45, $CH_3OH$).

EXAMPLE 8 cis(+)3-[4,6-Dihydroxychroman-3-ylmethyl]-4-methoxyanilline

A. The title compound of Example 4 or 5 (77 g, 99 mmol) was suspended in a mixture of ethyl acetate (770 mL) and saturated sodium bicarbonate (250 mL) and stirred vigorously for 15 minutes. The layers were separated and the organic phase washed with saturated sodium bicarbonate (250 mL) and water (250 mL) and then treated with magnesium sulfate. The volume was reduced, under vacuum, to 390 mL. Methanol (390 mL) and $Pd(OH)_2$ (11.62 g, 50% water wet) were added to the mixture and the contents were hydrogenated at 40 psi for 2 hours. The reaction mixture was filtered through Celite and the solvent removed from the filtrate, under vacuum, to give the crude product as a pale pink solid (25.8 g, 86%). This solid was slurried in methanol (12 mL)/methylene chloride (129 mL) for 1 hour, filtered and dried under vacuum to give 22.57 g (88%) of the title compound as an off white solid [mp=195°–96° C., $[\alpha]D$=+ 122.3 (c=0.81, THF)]. Anal. Calc. for $C_{17}H_{19}NO_4$:C, 67.76; H, 6.36; N, 4.65. Found: C, 67.65; H, 6.37; N, 4.63.

B. Alternatively, the title compound of Example 6 was dissolved in Methanol and treated with $H_2$ in the presence of $Pd(OH)_2$, under the conditions described in Section A to yield the title product of this Example.

EXAMPLE 9 cis(+)3-[4-Hydroxy-6-(7-chloroquinolin-2-yl)methoxychroman-3-ylmethyl]-4-methoxyanilline To a solution of the title compound of Example 8 (25g, 83 mmol) in dimethylformamide (DMF) (125mL) was added potassium t-butoxide (9.775 g, 87 mmol) in one portion. The reaction mixture was stirred for 1 hour, 7-chloroquinolin-2-ylmethyl chloride (17.6 g, 83 mmol) in DMF (125mL) was added dropwise over 2 hours and the reaction mixture stirred for an additional 18 hours. Ethyl acetate (300 mL) and water (1250 mL) were added to the reaction mixture which was stirred 15 minutes and filtered through Celite. The phases were separated and the aqueous phase was reextracted with ethyl acetate (300 mL). The combined organic extracts were washed two times with 500 mL of water, two times with 500 mL of aqueous sodium carbonate (20% solution) and once with brine (500 mL) and then treated with magnesium sulfate. The solvent was removed, under vacuum, to give a light yellow solid residue (38.2 g, 96%). The residue was repulped in methanol (79 mL) and isopropyl ether (711 mL) for 18 hours. The title compound was recovered after filtration, and drying, as a white solid. Yield 31.2 g (79%). $^{13}C$ NMR ($CDCl_3$) δ 159.5, 152.0, 150.3, 149.0, 147.8, 140.4, 136.7, 135.5, 128.9, 128.2, 127.9, 127.4, 125.9, 124.2, 119.3, 118.5, 117.5, 117.1, 116.0, 114.2, 112.2, 71.5, 65.4, 64.5, 56.3, 40.3, 27.0.

EXAMPLE 10 cis(+)3-[4-Hydroxy-6-95,6-difluorobenzothiazol-2-yl)methoxychroman-3-yl methyl]4-methoxyanilline Potassium t-butoxide (1.56g, 14 mmol) was added in one portion to a solution of the title compound of Example 8 (4 g, 13.2 mmol) in DMF (20 mL) at 23° C. The contents were stirred for 1 hour. A solution of 5,6-difluorobenzothiazol-2-ylmethyl chloride ("the chloride") (2.92 g, 13.2 mmol) in DMF (20 mL) was added over 1 hour and the reaction mixture stirred for an additional 18 hours. Potassium t-butoxide (298 mg, 2.6 mmol) was again added in one portion and the contents stirred for 1 hour. Additional chloride (583 mg, 2.6 mmol) was added in one portion and the contents stirred for 1 hour. Ethyl acetate (50 mL) and water were added to the reaction mixture which was stirred 15 minutes and filtered through Celite. The phases were separated and the aqueous phase was reextracted with ethyl acetate (50 mL). The combined organic extracts were washed two times with 50 mL water, two times with 50 mL aqueous sodium carbonate (20% solution), once with brine (50 mL) and then treated with magnesium sulfate. The solvent volume was reduced, under vacuum, to 20 mL. Hexanes (60 mL) was added, dropwise, to the extract and a precipitate was formed. The mixture was stirred for 18 hours. The precipitate was recovered by filtration and dried to give a tan solid (5.84 g, 91%). The precipitate was repulped in isopropanol (29 mL) for 18 hours, recovered by filtration and dried to yield 4.51 g (70%) of the title compound as a light yellow solid.

I claim:

1. A process for preparing the compound of the formula

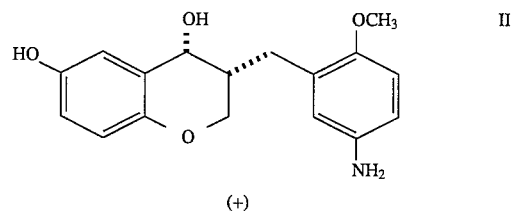

which comprises treating the compound of the formula

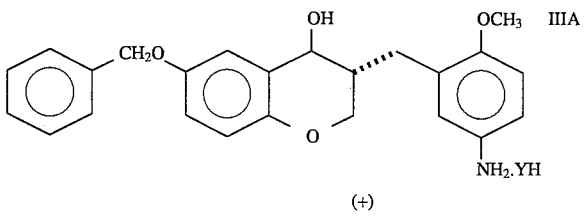

wherein YH is (R)-CSA or L-DTTA, with a base to form the compound of the formula

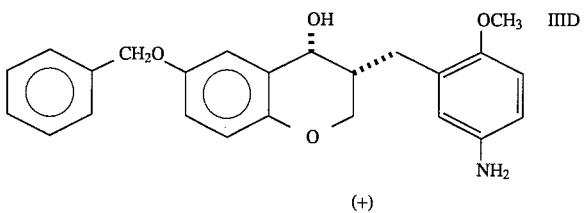

and treating the compound of the formula IIID with hydrogen in the presence of a noble metal catalyst.

2. The process of claim 1 wherein said catalyst is $Pd(OH)_2$.

3. The process of claim 1 wherein YH is L-DTTA.

4. The process of claim 1 wherein YH is (R)-CSA.

5. The process of claim 3 wherein the compound of formula IIIA is prepared by treating the compound of the formula

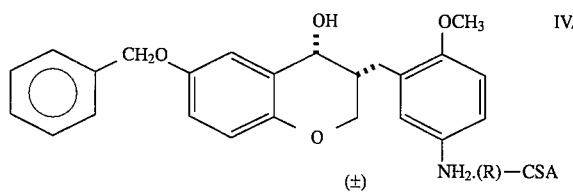

IVA (±) NH₂.(R)—CSA a) when YH is L-DTTA,
  i) with a base to form the compound of the formula

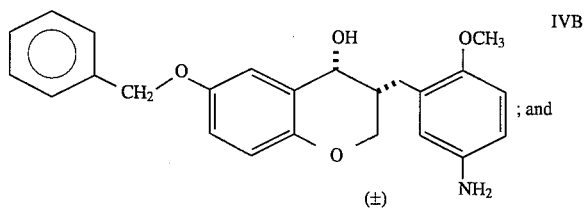

IVB (±) NH₂; and ii) treating the compound of the formula IVB with L-DTTA; or b) when YH is (R)-CSA, with hot aqueous acetone and recovering the product from the acetone solution by cooling and filtration, 6. The process of claim 5 wherein the compound of formula IVA is prepared by treating the compound of the formula

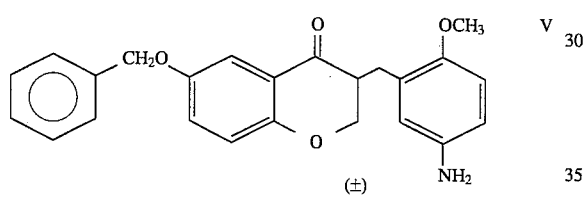

V (±) NH₂ with a reducing agent selected from NaBH₄/CeCl₃ or lithium tri-sec-butyl borahydride to form the the compound of the formula IVB and then treating the compound of the formula IVB with (R)-CSA to form the compound of the formula IVA 7. The process of claim 6 wherein said reducing agent is lithium tri-sec-butyl borohydride.

8. A process for preparing the compound of the formula

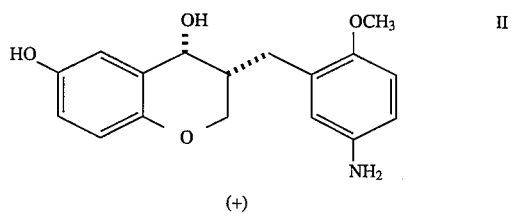

II (+) NH₂ which comprises the steps of
a) treating the compound of the formula

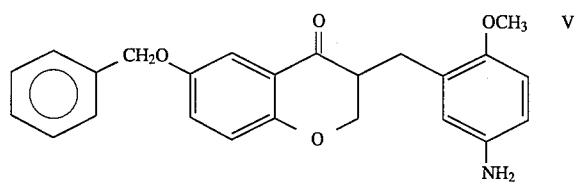

V NH₂ with a reducing agent selected from lithium tri-sec-butyl borohydride and NaBH₄/CeCl₃, and treating the resultant product with (R) camphorsulfonic acid to form the compound of the formula

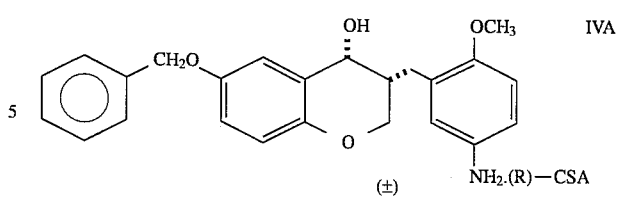

IVA (±) NH₂.(R)—CSA b) preparing the compound of the formula

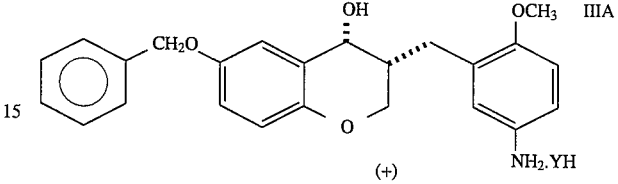

IIIA (+) NH₂.YH wherein YH is L-DTTA or (R)-CSA, by treating the compound of formula IVA, 1) when YH is L-DTTA
    i) with a base to form and the compound of formula

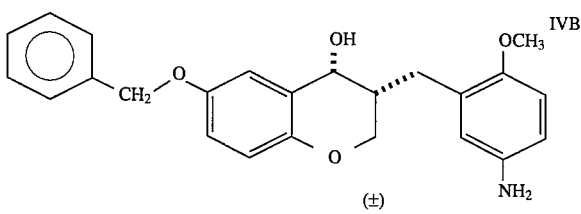

IVB (±) NH₂ and ii) treating the compound of formula IVB with ditoluyl-L-tartaric acid to form the compound of the formula

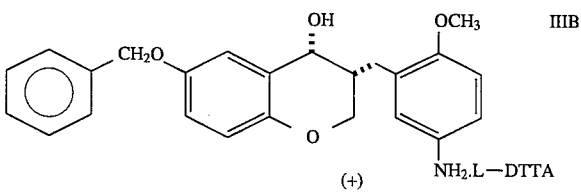

IIIB (+) NH₂.L—DTTA or 2) when YH is (R)-CSA, with hot acetone and cooling the hot acetone solution to yield, after filtration, the compound of the formula

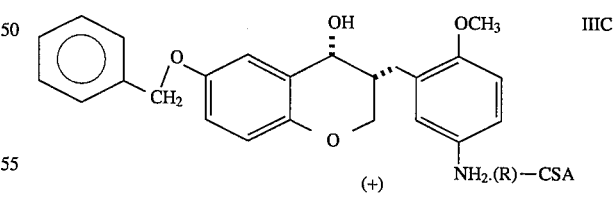

IIIC (+) NH₂.(R)—CSA and c) treating the compound of formula IIIA, wherein YH is as defined above, with a base to form the compound of the formula IIID in such formula IIID here followed by treatment of the compound of the formula IIID with H₂ hydrogen over a noble metal catalyst to form the compound of the formula II.

9. The process of claim 8 wherein said catalyst is Pd(OH)₂,

10. The compound of the formula

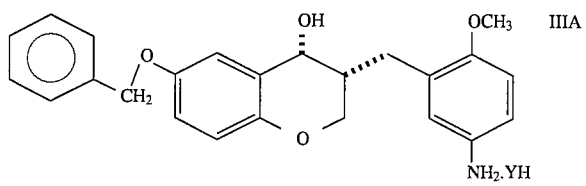

wherein YH is (R)-CSA, L-DTTA or is absent including the racemates and (+) forms with the proviso that when YH is L-DTTA the compound of formula IIIA is in the (+) form.

11. The compound of claim 10 wherein YH is L-DTTA.

12. The compound of claim 10 wherein YH is (R)-CSA and the compound is in the (+) form.

13. The compound of claim 10 wherein YH is (R)-CSA and the compound is present as the racemate.

14. The compound of claim 10 wherein YH is not present and the compound is in the (+) form 15. The compound of claim 10 wherein YH is not present and the compound is present as the racemate.

* * * * *